US011535881B2

(12) United States Patent
Mischler et al.

(10) Patent No.: US 11,535,881 B2
(45) Date of Patent: Dec. 27, 2022

(54) CONTINUOUS ANALYTE MONITORING ELECTRODE WITH CROSSLINKED ENZYME

(71) Applicant: Roche Diabetes Care, Inc., Indianapolis, IN (US)

(72) Inventors: Reinhold Mischler, Ludwigshafen (DE); Angelika Fuerst, Mannheim (DE); Daniel Kammerer, Heidelberg (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 202 days.

(21) Appl. No.: 16/484,900

(22) PCT Filed: Feb. 16, 2018

(86) PCT No.: PCT/EP2018/053917
§ 371 (c)(1),
(2) Date: Aug. 9, 2019

(87) PCT Pub. No.: WO2018/149981
PCT Pub. Date: Aug. 23, 2018

(65) Prior Publication Data
US 2019/0382819 A1    Dec. 19, 2019

(30) Foreign Application Priority Data
Feb. 17, 2017    (EP) ................................. 17156652

(51) Int. Cl.
*C12Q 1/00* (2006.01)
*G01N 27/327* (2006.01)

(52) U.S. Cl.
CPC ......... *C12Q 1/006* (2013.01); *G01N 27/3278* (2013.01); *C12Y 101/03004* (2013.01)

(58) Field of Classification Search
None
See application file for complete search history.

(56) References Cited

U.S. PATENT DOCUMENTS

2009/0014338 A1*  1/2009  Murata ................. C12Q 1/004
                                                     205/777.5

FOREIGN PATENT DOCUMENTS

| JP | 2000266716 | 9/2000 |
| JP | 2001006856 | 1/2001 |
| JP | 2006225744 | 8/2006 |
| JP | 2007010321 | 1/2007 |
| JP | 2008007719 | 1/2008 |
| JP | 2009031283 | 2/2009 |
| JP | 2010539515 | 12/2010 |
| RU | 0117011 U1 | 6/2012 |
| RU | 2489089 C2 | 6/2013 |
| WO | WO 97/27474 | 7/1997 |
| WO | WO 2009/153777 | 12/2009 |
| WO | WO-2009153777 A1 * 12/2009 ......... G01N 33/5438 |

OTHER PUBLICATIONS

Almeida et al. Electrochem. Acta (2012) 83: 311-320 (Year: 2012).*
Almeida et al. Electrochem. Acta (2010) 55: 8686-8695 (Year: 2010).*
Pandy et al. Langmuir (2007) 23: 3333-3337 (Year: 2007).*
Shi et al. Anal. Chem. (2004) 76: 632-638 (Year: 2004).*
Holland et al. J. Am. Chem. Soc. (2011) 133: 19262-19265 (Year: 2011).*
Yang et al. (lectrochem. Commun. (2006) 8: 665-672). (Year: 2006).*
Mizutani: "Application of Enzyme-modified Electrodes to Biosensors", Bunseki Kagaku. 1999, vol 48, No. 9, p. 809-822.
Bharathi et al: "A glucose biosensor based on electrodeposited biocomposites of gold nanoparticles and glucose oxidase enzyme", Analyst, Royal Society of Chemistry, vol. 126, No. 11, Nov. 1, 2001, pp. 1919-1922.
Huaan Zhong et al: "In situ chemo-synthesized multi-wall carbon nanotube-conductive polyaniline nanocomposites: Characterization and application for a glucose amperometric biosensor", Talanta, Elsevier, Amsterdam, NL, vol. 85, No. 1, Mar. 17, 2011, pp. 104-111.
Omer Yehezkeli et al: "Integrated Oligoaniline-Cross-Linked Composites of Au Nanoparticles/Glucose Oxidase Electrodes: A Generic Paradigm for Electrically Contacted Enzvme Systems", Chemistry—A European Journal, vol. 15, No. 11, Mar. 2, 2009, pp. 2674-2679.
Gun et al.: "Field-effect Nanoparticle-based Glucose Sensor on a Chip: Amplification Effect of Colmmobilized Redox Species", Electroanalysis, vol. 20, No. 16, 2008, pp. 1748-1753.
Zhang et al.: "Gold Nanoparticle-based Mediatorless Biosensor Prepared on Microporous Electrode", Electroanalysis, vol. 18, No. 3, 2006, pp. 217-222.

* cited by examiner

*Primary Examiner* — Susan M Hanley
(74) *Attorney, Agent, or Firm* — Woodard, Emhardt, Henry, Reeves & Wagner, LLP

(57) ABSTRACT

The present invention relates to an enzymatic electrode comprising a conductive surface and wherein a conjugate comprising at least one enzyme molecule is covalently bound to the conductive surface. The electrode is suitable for continuous analyte monitoring, particularly for continuous glucose monitoring (CGM) with glucose oxidase (GOD) as enzyme molecule. Further, the invention relates to an electrochemical sensor for measuring the concentration of an analyte, e.g. glucose under in vivo conditions comprising the enzymatic electrode.

17 Claims, 4 Drawing Sheets

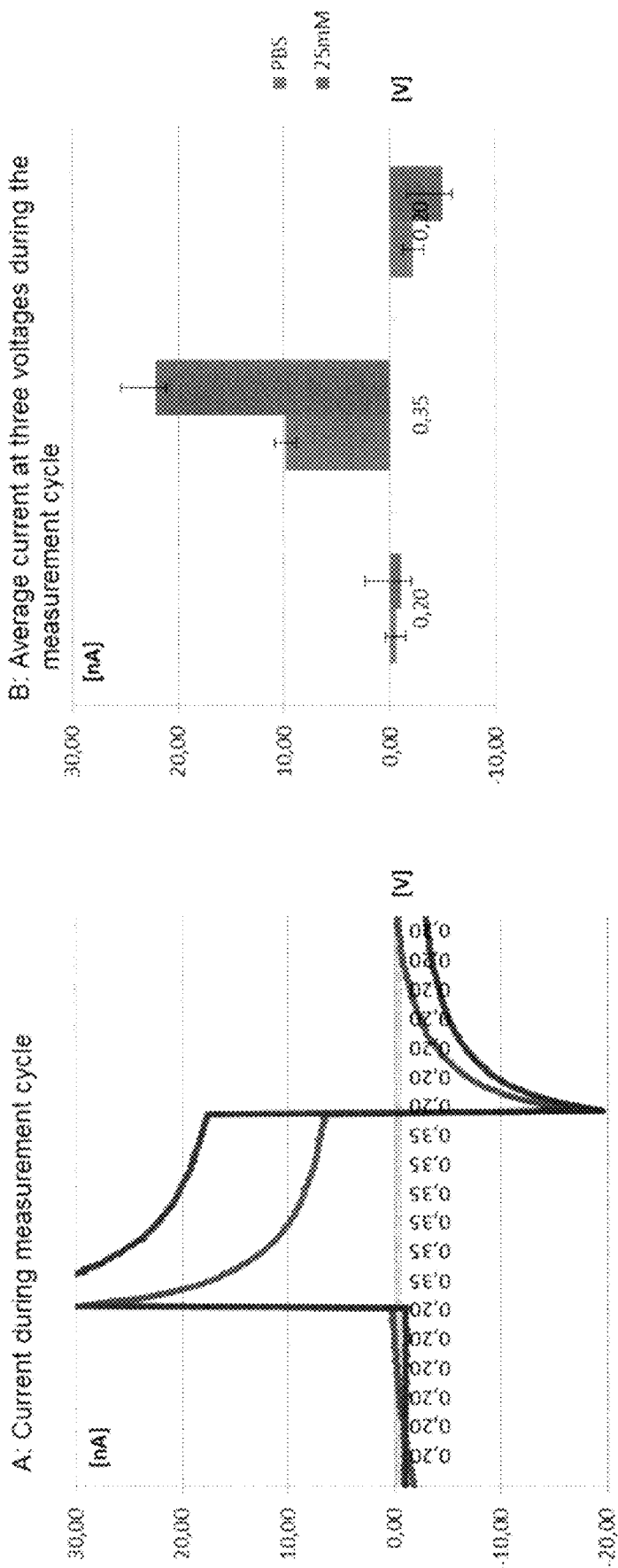

CONTINUOUS ANALYTE MONITORING ELECTRODE WITH CROSSLINKED ENZYME

The present invention relates to an enzymatic electrode comprising a conductive surface and wherein a conjugate comprising at least one enzyme molecule is covalently bound to the conductive surface. The electrode is suitable for continuous analyte monitoring, particularly for continuous glucose monitoring (CGM) with glucose oxidase (GOD) as enzyme molecule. Further, the invention relates to an electrochemical sensor for measuring the concentration of an analyte, e.g. glucose under in vivo conditions comprising the enzymatic electrode.

Non-fluidic sensors with implantable or insertable electrodes facilitate the measurement of physiologically significant analytes such as, for example, lactate or glucose in a patient's body. In many cases, the electrodes of non-fluidic sensors are coated with electrically conductive layers in which enzyme molecules are bound. The enzyme molecules may catalyze a redox reaction, thereby generating an electrically detectable signal. This type of sensor is designated enzymatic non-fluidic (ENF) sensor.

A sensor for the measurement of glucose may comprise, for example, the enzyme GOD (EC 1.1.3.4), which catalyzes the conversion of the analyte glucose to gluconolactone. In the absence of a synthetic redox mediator, the co-substrate oxygen $O_2$ is converted to hydrogen peroxide $H_2O_2$ on the sensor's surface. The generated $H_2O_2$ may be catalytically decomposed to $H_2O$, resulting in an electrical current which correlates to the glucose concentration.

Known sensors often suffer from disadvantages in that the generation of $H_2O_2$ in the catalytic site of the enzyme and its decomposition on the electrode surface are spacially separated. Thus, the conversion rate of $H_2O_2$ at the working electrode is inefficient. Further, an extended presence of $H_2O_2$ in the enzyme layer may inactivate the enzyme molecules.

U.S. Pat. No. 6,284,126 B1 discloses a sensor comprising hydrogel-encapsulated enzyme molecules applied to the surface of an electrode. Hydrogel-encapsulated enzymes, however, suffer from the further disadvantage that the gel swells in contact with aqueous media. This may cause amperometric measurement signal changes over the whole swelling time leading to a sensor drift.

In other types of sensors, the enzyme layer additionally comprises a synthetic redox mediator. In order to avoid a sensor drift, the redox mediator and the enzyme have to be covalently incorporated into a polymeric structure. This, however, leads to an inefficient electron transfer from the enzyme to the mediator since mobility of those compounds is limited due to their incorporation into the polymeric structure. Consequently, hydrogen peroxide formation on the enzyme competes with the electron transfer to the mediator leading to an oxygen dependency. In addition, swelling processes of the polymeric structures may cause a disturbance.

Another known sensor, e.g. as described in EP 2 348 964 B1 comprises an electrode coated with an enzyme layer, which is a conductive paste comprising a polymeric binder, carbon particles, enzyme molecules, and a catalytic redox mediator applied to an electrode surface. However, a disadvantage thereof is the time delay for achieving a stable operational state since this type of enzyme layer has to be completely wetted and polarized. Further, a paste-based enzyme layer is brittle and thus cannot be applied over larger areas on the electrode surface, particularly when the sensor body has a curved shape.

WO 2009/153777 discloses an electrode comprising a conductive surface and a matrix bound thereto, wherein the matrix comprises at least two species of compounds, namely, at least one species of enzymes and at least one species of metal nanoparticles, wherein the components are covalently bound to one another through first binding moieties and the matrix is covalently bound to the surface through one or more same or different second binding moieties. The matrix may be bound to the surface by forming a layer of a reactive compound on the conductive surface and contacting the layered conductive surface with nanoparticles and enzyme molecules, both of which containing reactive groups and subsequently electropolymerizing the compounds in the layer to cause binding of the reactive groups to one another to form the matrix.

This electrode structure of WO 2009/153777 has certain disadvantages in that its manufacture by electropolymerization is complex since it requires several steps including chemical modification of metal nanoparticles. Due to this complexity, the process is prone to a lack of reproducibility.

Thus, it was an object of the present invention to provide an efficient enzyme electrode, which can be manufactured easily and reproducibly. This object is achieved by providing a composition of enzyme molecules which are covalently bound to nanoparticles and the electrode surface, but wherein the metal nanoparticles are not covalently bound to the electrode surface.

A first subject-matter of the present invention is an electrode comprising a conductive surface and a conjugate comprising at least one enzyme molecule and at least one conductive nanoparticle covalently bound to each other, wherein the conjugate is covalently bound to the electrode surface via at least one enzyme molecule and wherein the nanoparticle is not covalently bound to the electrode surface.

The electrode of the invention is coated with a conjugate comprising at least one enzyme molecule and at least one conductive nanoparticle. Preferably, the conjugate comprises a single enzyme molecule and at least one conductive nanoparticle.

Typically, the enzyme molecule is an oxidoreductase, i.e. an enzyme molecule catalyzing a redox reaction. Particularly, the enzyme catalyzes a redox reaction wherein $H_2O_2$ is generated and/or consumed. More particularly, the enzyme catalyzes a reaction wherein $H_2O_2$ is generated, e.g. from $O_2$ as a co-substrate. Specific examples of such enzymes are glucose oxidase (EC 1.1.3.4), hexose oxidase (EC 1.1.3.5), cholesterol oxidase (EC 1.1.3.6), galactose oxidase (EC 1.1.3.9), alcohol oxidase (EC 1.1.3.13), (S)-2 hydroxy acid oxidase (EC 1.1.3.15), L-glutamate oxidase (EC 1.4.3.11)), or L-aspartate oxidase (EC 1.4.3.16). Particularly, the enzyme molecule is glucose oxidase, e.g. glucose oxidase from *Aspergillus* or *Penicillum*.

According to the present invention, at least one enzyme molecule of the conjugate is covalently bound to both the conductive surface of the electrode and to at least one conductive nanoparticle. The covalent binding to the surface and to a nanoparticle may occur via the same or different functional groups. In some embodiments, the binding occurs via the same functional groups. For example, the binding may occur via sulfur-containing functional groups, particularly via sulfide or disulfide groups which may form covalent bonds to the conductive surface of the electrode and to a nanoparticle.

In some embodiments, the enzyme molecule comprises two or more amino acid residues with a sulfur-containing side chain which may directly bind to the electrode surface and/or a nanoparticle, e.g. a cysteine residue comprising a sulfide (SH) group or a cysteine bridge comprising a disulfide group (—S—S—). In different, usually more preferred embodiments, the enzyme molecule has been modified by incorporating one or more sulfur-containing functional groups, particularly sulfide or disulfide groups. Modification may involve functionalizing primary amino groups on the enzyme molecule, e.g. the amino terminus and/or amino side chain groups of amino acid residues within the enzyme molecule, e.g. amino side chain groups of lysine and/or arginine residues, particularly amino acid side chain groups of lysine residues. In other embodiments, modification may involve functionalizing the carboxy terminus and/or carboxy side chain groups of aspartate and/or glutamate residues.

Modification of an enzyme molecule may be performed by using a functionalization reagent comprising a group capable of modifying a polypeptide, e.g. an amino-reactive group or a carboxy-reactive group. Further, the functionalization reagent comprises a functional group, e.g. a sulfur-containing functional group, or a group to which a functional group, e.g. a sulfur-containing functional group may be attached. Preferably, a reagent is used comprising an amino-reactive group selected e.g. from an NHS ester, isocyanate, isothiocyanate, and a sulfur-containing functional group, e.g. a sulfide or disulfide group. The functional group may be directly connected to the amino-reactive group or be connected to the amino-reactive group via a spacer, which may have a chain length of 1 to 5, e.g. 1 to 3 atoms. An especially preferred amino-reactive reagent containing a sulfur-containing functional group is 3,3'-dithiodipropionic acid di(N)-hydroxysuccinimide ester (DSP), also known as Lomant's reagent.

Introduction of functional groups may involve a reaction of the enzyme molecule with the functionalization reagent under conditions wherein surface-exposed side chains of the enzyme molecule are functionalized. By adjusting the molar ratio of enzyme molecule and functionalization reagent, the functionalization degree of the enzyme molecule may be adjusted. Typically, the molar ratio of enzyme molecule and functionalization reagent is about 1:1 or higher, e.g. about 1:1 to about 1:10, about 1:1 to about 1:2, about 1:2 to about 1:5, or about 1:5 to about 1:10.

The conjugate used for coating the electrode also comprises at least one conductive nanoparticle, i.e. a nanoparticle having a conductive surface or consisting of conductive material. The nanoparticle may be a metal nanoparticle, e.g. a particle of platinum, palladium, iridium, gold, silver, or any alloy thereof. Particularly, the nanoparticle is capable of catalytically decomposing $H_2O_2$, e.g. a platinum or palladium nanoparticle. Typically, the nanoparticles may have an average size of 100 nm or less, e.g. an average size of 1 nm to 50 nm or 5 nm to 15 nm as measured by dynamic light scattering.

The conjugate of enzyme molecules and nanoparticles may be obtained by providing an enzyme molecule having at least one functional group, e.g. a sulfur-containing functional group, particularly a sulfide and/or disulfide group, and reacting the enzyme molecule with a nanoparticle under conditions where a covalent bond between an enzyme molecule and a nanoparticle may be formed. The nanoparticles as such do not contain functional groups which are capable of forming a covalent bond with the electrode surface. The respective amounts of the reactants may be adjusted in that the conjugates comprise enzyme molecules and nanoparticles in a molar ratio of enzyme molecules: nanoparticles of about 1:1 to about 1:3, particularly of about 1:1 to about 1:2.

A conjugate formed by the reaction comprises at least one enzyme molecule which is conjugated to at least one nanoparticle, wherein at least one free functional group is present on an enzyme molecule in the conjugate. The average size of the conjugate may range from about 10 nm to about 300 nm, e.g. about 50 nm to about 100 nm as measured by dynamic light scattering.

According to the present invention, the conjugate as described above is applied to the conductive surface of an electrode, wherein a free functional group on an enzyme molecule of the conjugate forms a covalent bond with the electrode surface.

The conductive surface of the electrode may be a metal surface such as, for example, gold, platinum, palladium, iridium, silver, or an alloy thereof. The conductive surface may also be a metal oxide surface such as an indium-tin oxide surface or a graphite surface. Particularly, the surface is a gold surface.

The conjugate forms an enzyme layer on the electrode surface. For practical applications, this enzyme layer may be covered by a further polymer layer which presents a diffusion resistance to the analyte to be measured and therefore acts as a diffusion barrier. The diffusion barrier may, for example, comprise block copolymers with alternating hydrophilic and hydrophobic blocks as described in EP 2 697 388 B1. The diffusion barrier may extend continuously essentially over the entire area of the conductive surface of the electrode. On the diffusion barrier, a further bio-compatible membrane may be arranged as spacer that establishes a minimal distance between the enzyme layer on the electrode and cells of surrounding body tissue. This means advantageously generates a reservoir from which analyte molecules can reach the corresponding enzyme layer in case of a transient disturbance of the fluidic change in the surroundings of an enzyme layer. Preferred spacers made from copolymers of (meth)acrylates are described in EP 2 697 388 B1.

In some embodiments, the conjugate may additionally comprise other components, e.g. a synthetic redox mediator. In other usually more preferred embodiments, the conjugate does not comprise a synthetic redox mediator. In still other usually preferred embodiments, the conjugate essentially consists or consists of at least one enzyme molecule and at least one nanoparticle, particularly of a single enzyme molecule and at least one nanoparticle, e.g. 1 or 2 nanoparticles.

Further, the present invention refers to an electrochemical sensor for measuring the concentration of an analyte comprising at least one electrode as described above.

The sensor of the invention is suitable for measuring the concentration of an analyte under in vivo conditions, e.g. in tissue, skin, or a body fluid. The sensor is particularly suitable for intracutaneous or subcutaneous measurement.

The analyte may be any type of compound which may be measured within the body, e.g. within tissue and/or body fluid. Examples of analytes include endogenous analytes, i.e. compounds which are produced within the body or exogenous analytes, e.g. analytes which have been introduced into the body. For example, the analytes may be selected from saccharides, acids including fatty acids and amino acids, peptides, proteins, salts, and gases. Of interest are glucose, urea, glycerol, lactate, pyruvate, oxygen, carbon dioxide, sodium cations, and chloride ions. Of particular interest are analytes which can be oxided or reduced under formation of $H_2O_2$ such as glucose, lactate, cholesterol, hexose, glactose, or alcohol.

The sensor of the invention is suitable for short term or long term measurement. The sensor is particularly suitable for repeated e.g. continuous monitoring of one or more analytes for a longer time period of 3 to 12 months or for a shorter period of time of 3 to 14 days.

The sensor of the invention is an electrochemical sensor comprising at least one electrode and respective circuitry. More particularly, the sensor is an amperometric electrochemical sensor comprising at least one working electrode comprising a conductive surface to which a conjugate as described above is covalently bound. Typically, the sensor comprises at least one further electrode, particularly a counter electrode and/or a reference electrode. The working electrode is sensitive for the analyte to be measured at a polarization voltage which is applied between working and reference electrodes and which may be regulated by a potentiostat. A measurement signal may be provided as an electric current between the counter electrode and the working electrode. In some embodiments, a separate counter electrode is absent and a pseudo reference electrode is present, which also works as a counter electrode. Thus, a sensor for an analyte typically comprises a set of at least two, preferably of three electrodes. In a particular embodiment, the enzyme molecule is bound to the conductive surface of the working electrode only.

In a further particular embodiment of the invention, the enzyme molecule is glucose oxidase, e.g. a chemically modified glucose oxidase as described above, and the analyte is glucose. In this embodiment, an electrochemical sensor for measuring the concentration of glucose is provided. More particularly, a sensor for continuous glucose measurement is provided.

A further aspect of the invention relates to a method of manufacturing an electrode as described above comprising the steps:
  a) preparing a conjugate of at least one enzyme molecule and at least one nanoparticle under conditions wherein the enzyme molecule in the conjugate has free functional groups for covalently binding to a conductive surface of the electrode and the nanoparticle in the conjugate does not have free functional groups for covalently binding to the conductive surface, and
  (b) covalently binding said conjugate to the conductive surface of an electrode, wherein the binding exclusively occurs via free functional groups on the enzyme molecule.

Still a further subject of the invention is a method of measuring an analyte, e.g. glucose in a medium, e.g. under in vivo conditions, particularly in tissue and/or in a body fluid of a subject, particularly of a human subject, comprising using an electrode or an electrochemical sensor as described above. Alternatively, the method of the invention also encompasses measurement of an analyte under in vitro conditions, e.g. in a sample of a body fluid obtained from a subject, particularly from a human subject.

Further, the present invention is described in the context of the following figures and examples.

FIG. 4 shows the results from three different measurements of a working electrode to which a GOD-Pt nanoparticle conjugate has been bound (A): Current during measurement cycle at three voltages (0.20 V-0.35 V-0.20 V). (B): Average current at three voltages during the measurement cycle.

Figure 1:
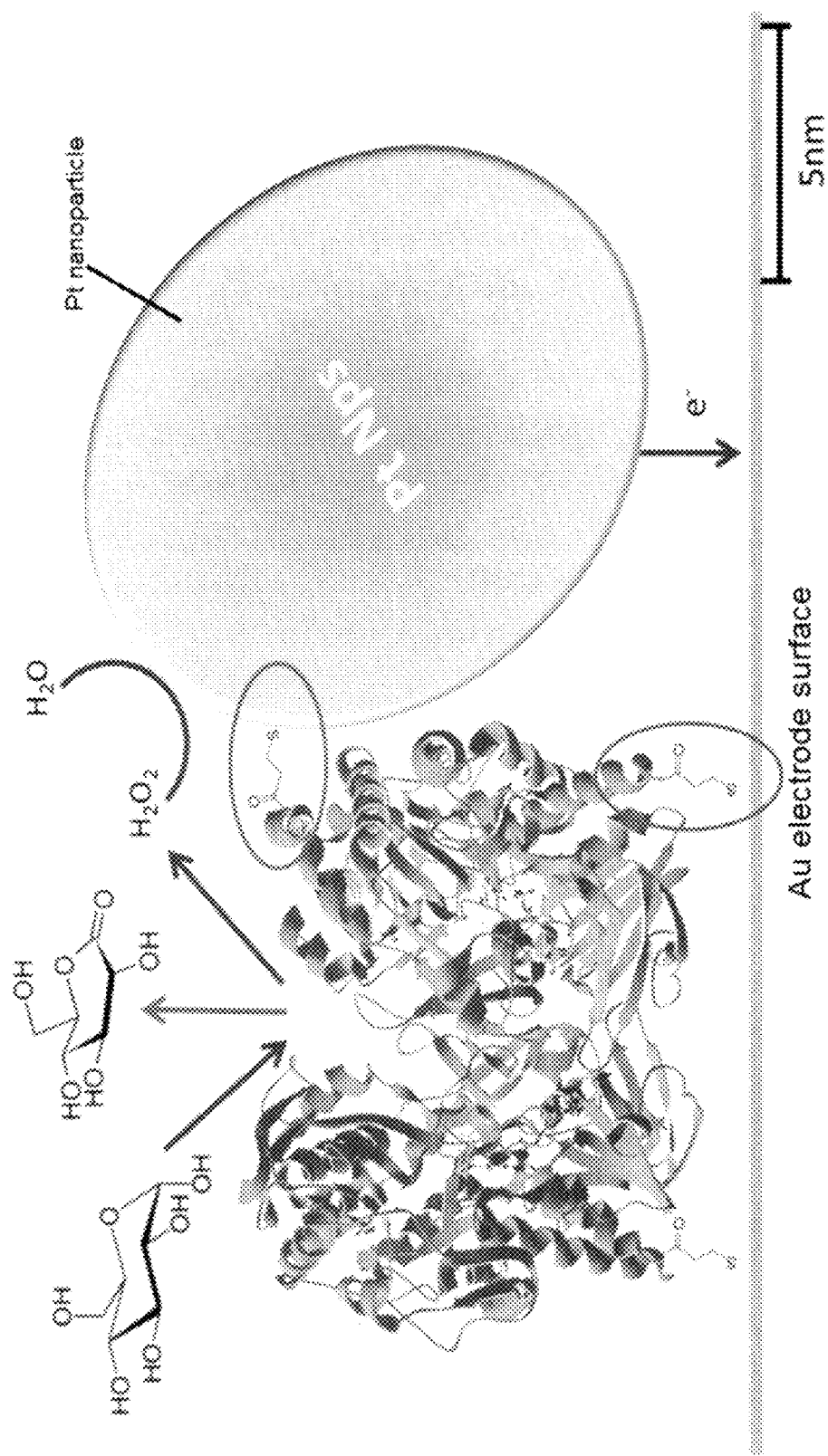
FIG. 1 shows an exemplary embodiment of a working electrode according to the invention.

In FIG. 1, an exemplary embodiment of a working electrode for the measurement of glucose is shown. To an electrode surface, e.g. an Au electrode surface, an enzyme molecule is covalently bound via a sulfur-containing functional group. Further, the enzyme molecule is covalently bound via another sulfur-containing functional group to at least one nanoparticle, e.g. a Pt nanoparticle.

The enzyme molecule is a glucose oxidase which has been modified at surface exposed amino side chain groups with Lomant's reagent, thereby generating sulfur-containing functional groups. Glucose oxidase catalyzes the oxidation of glucose to gluconolactone, thereby generating $H_2O_2$. A catalytic decomposition of $H_2O_2$ to $H_2O$ occurs on the nanoparticle, resulting in a flux of electrons ($e^-$). Thereby, an electric current is generated, the strength of which correlates to the glucose concentration.

The electrode of the present invention uses the naturally occurring mediator system $O_2/H_2O_2$. A synthetic redox mediator is absent. The generated $H_2O_2$ is efficiently decomposed to $H_2O$ in the presence of the catalytic nanoparticle.

Due to the covalent coupling of the catalytic nanoparticles and enzyme molecules to the working electrode, a loss of molecules from the enzyme layer can be avoided. Further, no transition resistance between the enzyme layer and the electrical conductor of the working electrode will occur due to the presence of a conductive metal nanoparticle.

Thus, the electrode of the invention and a sensor comprising said electrode provide a simple and efficient construct, which can easily be manufactured by applying a conjugate of nanoparticles and functionalized enzyme to the conductive surface of the electrode.

EXAMPLE 1

Coupling of Platinum Nanoparticles to Glucose Oxidase

Glucose oxidase (GOD) from *Aspergillus niger* has three cysteine residues. Cysteine residue 164 forms a cysteine bridge to cysteine residue 206 and the third cysteine residue 521 is not exposed to the surface. Thus, the GOD was biochemically modified with functional sulfide, namely with Lomant's reagent DSP (3,3'-dithiodipropionic acid di(N)-hydroxysuccinimide ester) available from Sigma Aldrich. The N-hydroxysuccinimide ester group reacts with surface exposed lysine side chains of GOD, thereby introducing sulfur-containing groups into the enzyme molecule.

Several samples of sulfide-modified GOD with different molar ratios of GOD to Lomant's reagent, were prepared by incubating the compounds in molar ratios of GOD:DSP of 1:1, 1:10, 1:100, and 1:200 for 30 min at room temperature. The reaction products were analyzed by non-reducing polyacrylamide electrophoresis as shown in FIG. 2.

Already at a molar ratio of 1:1, cross-linking of GOD molecules was observed. At a ratio of 1:200, nearly all GOD molecules were cross-linked and high molecular weight aggregates were formed. As a control, GOD without DSP was used.

Figure 2:
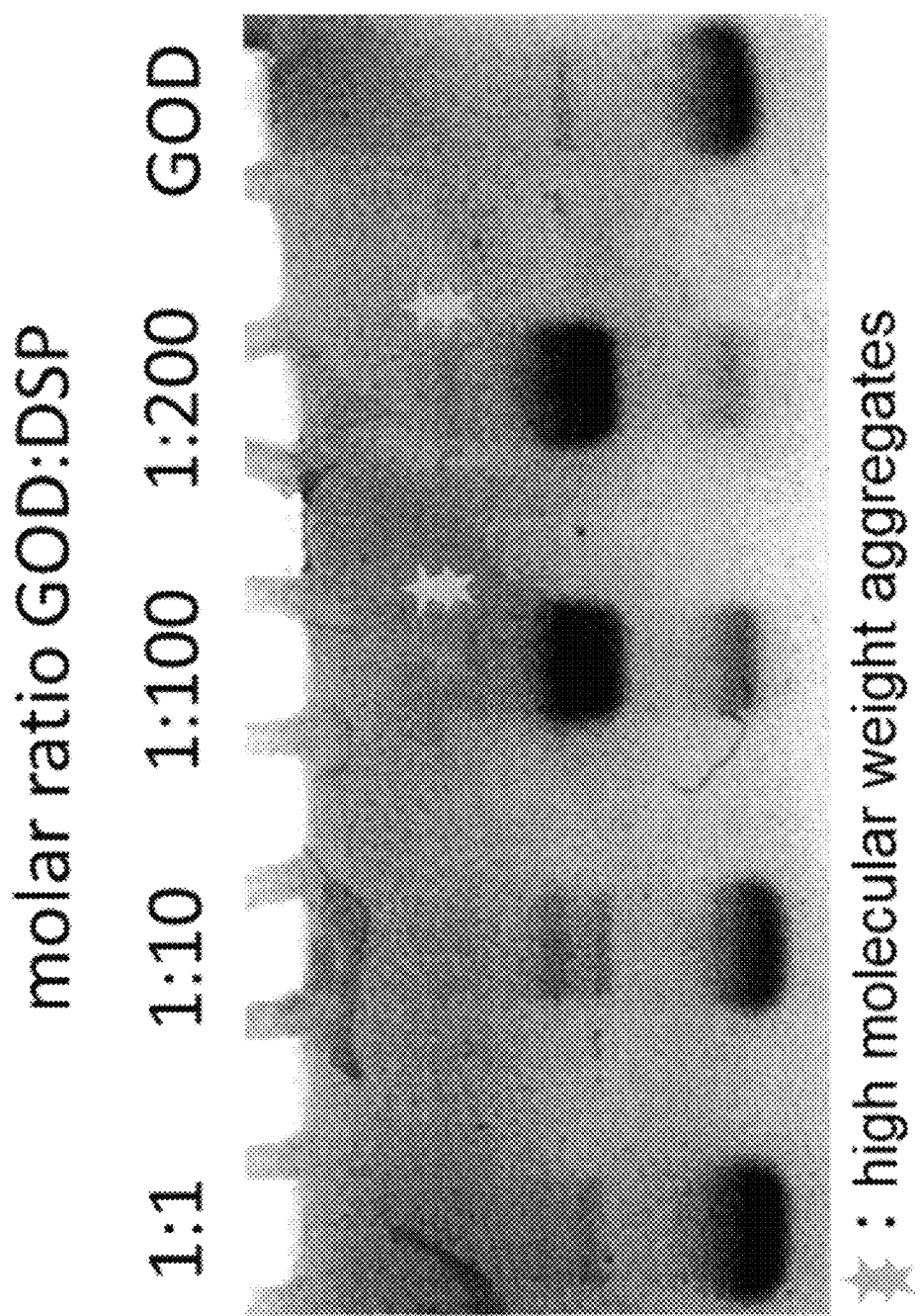
FIG. 2 shows a non-reducing polyacrylamide gel electrophoresis of reaction mixtures of glucose oxidase (GOD) and Lomant's reagent (DSP) and different molar ratios.

To all samples from FIG. 2, 1 ml of a nanoplatinum dispersion (0.5 mg/ml; particle size<15 nm) was added and incubated for 12 h overnight at room temperature according to Cao et al. (Biosens. Bioelectron. 26(2010), 87-91) in order to achieve covalent binding of the particles to the sulfide group-modified GOD.

Figure 3:
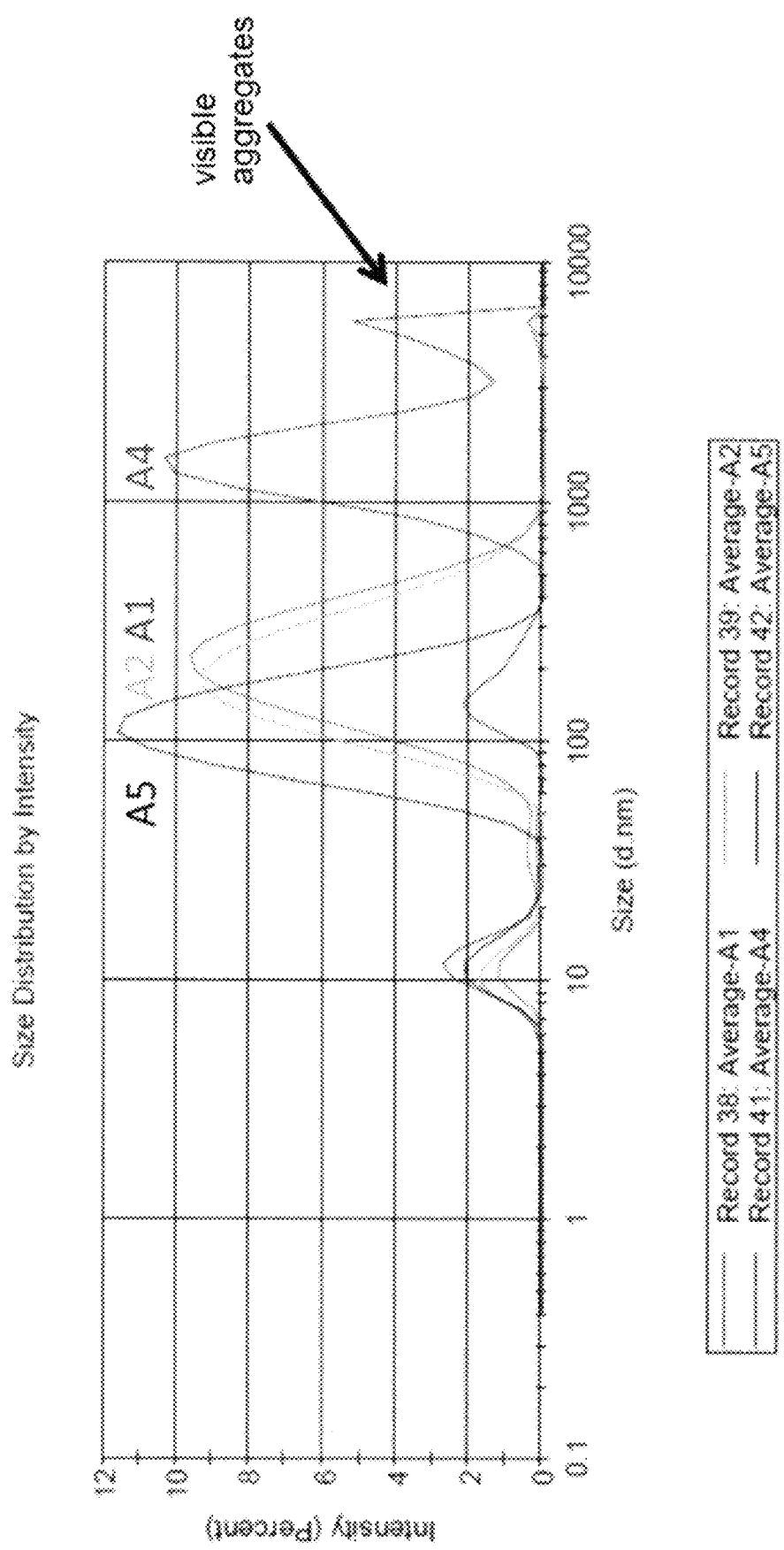
FIG. 3 shows the size distribution of different conjugates of GOD and platinum nanoparticles measured by dynamic light scattering.

On the next day, the samples were measured by dynamic light scattering (DLS) to determine the size of the cross-linked particles. The results are shown in FIG. 3.

In sample A3 (molar ratio of GOD:DSP=1:100) and sample A4 (molar ratio of GOD:DSP=1:200), aggregates could be detected visually. These large particles have a size above the measuring range of the DLS apparatus of 10 µm and are shown as cut off peak.

Control sample A5 (unmodified GOD) exhibits two discreet peaks. Samples A1 (molar ratio GOD:DSP=1:1) and A2 (molar ratio GOD:DSP=1:10) have an increased particle size compared to control sample A5, which is an indication that conjugates of GOD molecules and Pt nanoparticles have been obtained.

EXAMPLE 2

Electrode Coating

Gold chips QFX301 (LOT Darmstadt) were used as a base for the working electrode. For the subsequent measurement, a sensor set-up with three electrodes, a working electrode, a reference electrode, and a counter electrode (Melinex gold film) was used.

80 µl of the reaction mixture of sample A2 from Example 1 were pipetted onto the working electrode gold chip and incubated for 10 min at room temperature in order to obtain a covalent coupling of free sulfide groups on the conjugates with the gold surface. After incubation, unbound material was removed by several dippings into phosphate buffered saline (PBS).

EXAMPLE 3

Glucose Measurement

The sensor of Example 2 was tested with a Gamry potentiostat (C3 Analysentechnik München). For this purpose, a chronoamperometric measurement with three voltage levels (200 mV, 350 mV, 200 mV) was performed, at which the resulting current was measured each time for 10 mins. The measurements were conducted in a PBS solution as control and 26 mM glucose. The results are shown in FIG. 4.

At a preset voltage of 0.20 V, no significant difference between the solutions was found. At 0.35 V, an increase in current was found in both solutions, wherein the current in 26 mM glucose was significantly higher compared to PBS (FIG. 4A). This result demonstrates that the coated working electrode is sensitive to glucose. The average electric current during the last five minutes of measurement at the three voltage levels (0.20 V, 0.35 V, 0.20 V) of the measurement cycle is shown in FIG. 4B. The significant difference in the measurement signals of PBS and 26 mM glucose at 0.35 V voltage is clearly observable. A notable sensor drift was observed only in the first minutes of measurement at a given voltage, showing that the sensor has a short calibration time.

The invention claimed is:

1. An electrode comprising a conductive surface and a conjugate comprising at least one enzyme molecule and at least one conductive nanoparticle covalently bound to each other, wherein the conjugate is covalently bound to the electrode surface via the at least one enzyme molecule and wherein the nanoparticle is not directly covalently bound to the conductive surface.

2. The electrode of claim 1, wherein the at least one enzyme molecule is an H2O2 generating and/or consuming enzyme molecule selected from the group consisting of a glucose oxidase (EC 1.1.3.4), a hexose oxidase (EC 1.1.3.5), an (S)-2 hydroxy acid oxidase (EC 1.1.3.15), a cholesterol oxidase (EC 1.1.3.6), a galactose oxidase (EC 1.1.3.9), an alcohol oxidase (EC 1.1.3.13), an L-glutamate oxidase (EC 1.4.3.11) and an L-aspartate oxidase (EC 1.4.3.16).

3. The electrode of claim 1, wherein the covalent binding of the at least one enzyme molecule to the electrode surface occurs via a sulfur containing functional group selected from the group consisting of a sulfide group and a disulfide group, and/or wherein the covalent binding of the at least one enzyme molecule to a nanoparticle occurs via a sulfur containing functional group selected from the group consisting of a sulfide group and a disulfide group.

4. The electrode of claim 1, wherein the at least one enzyme molecule has been modified to incorporate at least one functional group for covalent binding to the electrode surface and a nanoparticle, and wherein the at least one enzyme molecule has been modified at the amino terminus and/or at an amino side chain group.

5. The electrode of claim 4, wherein the at least one enzyme molecule has been modified by reacting the at least one enzyme with a functionalizing reagent in a molar ratio of enzyme to functionalization reagent of about 1:1 to about 1:10.

6. The electrode of claim 1, wherein the nanoparticles are metal nanoparticles selected from the group consisting of platinum, palladium, iridium, gold and silver nanoparticles.

7. The electrode of claim 1, wherein the nanoparticles have an average size of about 1 to about 100 nm.

8. The electrode of claim 1, wherein the conjugate has an average size of about 10 nm to about 300 nm.

9. The electrode of claim 1, wherein the conjugate does not contain a redox mediator.

10. The electrode of claim 1, wherein the electrode surface is a metal surface.

11. An electrochemical sensor for measuring the concentration of an analyte comprising at least one electrode according to claim 1.

12. The sensor of claim 11, wherein the enzyme molecule is a functionalized glucose oxidase, and the analyte is glucose.

13. The sensor of claim 11 for in vivo or in vitro use.

14. A method of manufacturing an electrode of claim 1, comprising the steps:
   (a) preparing a conjugate of at least one enzyme molecule and at least one nanoparticle under conditions wherein only the at least one enzyme molecule, but not the nanoparticle in the conjugate has free functional groups for covalently binding to a conductive surface of an electrode, and
   (b) covalently binding said conjugate to the conductive surface of the electrode, wherein the binding exclusively occurs via free functional groups on the at least one enzyme molecule.

15. A method of measuring an analyte in a tissue and/or a body fluid comprising using the electrode of claim 1.

16. A method of measuring an analyte in a tissue and/or a body fluid comprising using the electrochemical sensor of claim 11.

17. An electrode comprising:
a conductive surface; and
a conjugate comprising at least one enzyme molecule and at least one nanoparticle covalently bound to each other,
wherein the at least one enzyme molecule, and not the nanoparticle, has free functional groups covalently bound to the conductive surface.

* * * * *